United States Patent [19]

Hanotier

[11] 4,259,522

[45] Mar. 31, 1981

[54] PROCESS FOR THE PRODUCTION OF ISOPHTAHALIC ACID

[75] Inventor: Jacques D. V. Hanotier, Saint-Lambert, Belgium

[73] Assignee: Labofina S.A., Brussels, Belgium

[21] Appl. No.: 104,470

[22] Filed: Dec. 17, 1979

[51] Int. Cl.$^3$ .............................. C07C 51/265
[52] U.S. Cl. .................................... 562/412
[58] Field of Search ......................... 562/412

[56] References Cited

U.S. PATENT DOCUMENTS

| 2,723,994 | 11/1955 | Haefele | 562/412 |
| 2,833,819 | 5/1958 | Egbert | 562/412 |
| 2,833,820 | 5/1958 | Egbert | 562/412 |

*Primary Examiner*—Natalie Trousof
*Assistant Examiner*—Michael Shippen

[57] ABSTRACT

Process for producing isophthalic acid by direct oxidation of m-toluic acid or a mixture of m-toluic acid with m-xylene and partially oxidized intermediates under mild conditions without the presence of consumable organic solvents or corrosive bromine promoters comprising forming a homogeneous, aqueous mixture of said substrate containing from 10 to 80 weight percent water and an active catalyst comprising a manganese compound or a mixture of a maganese compound and a cobalt compound, the minimum concentration (M) of catalyst in said mixture in millimoles per kilogram of mixture being given by the equation $$M = \frac{(y + 45.9\,z)(x + 0.0967) + 9.50\,x}{3.02\,x}$$

wherein x is the mole fraction of maganese in the catalyst, y is the mole ratio of water to m-toluic acid and z is the ratio of dissolved isophthalic acid to m-toluic acid, the maximum concentration of catalyst being not more than about 40 millimoles catalyst per kilogram of mixture and reacting said substrate with a molecular oxygen-containing gas at a temperature from about 140° to 220° C. and a pressure sufficient to maintain water in the liquid phase.

11 Claims, 2 Drawing Figures

PROCESS FOR THE PRODUCTION OF ISOPHTAHALIC ACID

BACKGROUND OF THE INVENTION

This invention relates to a process for producing isophthalic acid by oxidation in aqueous medium of m-toluic acid or mixtures of m-toluic acid with m-xylene and/or other partially-oxidized derivatives thereof such as m-tolualdehyde.

Isophthalic acid is a valuable intermediate in the manufacture of polyester and alkyd resins. Used initially as a simple substitute for phthalic anhydride, it has progressively gained a self-established position based mainly upon the fact that it imparts to those resins better properties with respect to e.g. toughness and resistance to heat and chemical agents.

The widely used starting material for the manufacture of isophthalic acid is m-xylene. Generally, most processes suitable for the oxidation of p-xylene into terephthalic acid can be adapted to the transformation of m-xylene into isophthalic acid. Although such oxidizing agents as nitric acid or sulfur have been employed for this purpose, the most commonly used oxidant is molecular oxygen. In one process, m-xylene is reacted with air at high temperature and pressure in the presence of a lower alkanoic acid, e.g., acetic acid, as a solvent, a salt of at least one heavy metal, such as cobalt, manganese or cerium, as catalyst, and a bromine-containing compound as promoter.

Although this process is applied successfully at the commercial scale, it has some serious drawbacks. For instance, as a result of the combined action of the bromine promoter, the acidic solvent and the high temperature, the reaction mixture is highly corrosive. Consequently, expensive alloys or metals such as titanium must be employed as construction materials not only for the reactor itself but also for various parts of the downstream equipment, e.g., the heat exchangers to condense exit vapors and to some extent the centrifuge or any other solid-liquid separation device used to separate isophthalic acid. Another and still more serious drawback of this prior process arises from the fact that, under the severe oxidation conditions utilized, the acidic solvent undergoes substantial degradation which heavily impairs the economics of the process as the cost of petroleum-based chemicals increases.

In this bromine-promoted process, the reaction mixture must be maintained under "substantially anhydrous conditions", especially when the feed consists of "partially oxidized hydrocarbons such as toluic acid" (U.S. Pat. No. 3,064,044). This requires that the mother-liquor from the separation of the desired diacid be further fractionated to recover the alkanoic acid solvent in anhydrous form for recycle. The residue from this fractionation comprises the catalysts together with some by-products and untransformed intermediates. Generally, the residue is incinerated whereby the catalysts are converted to metal oxides which can only be reconverted into reusable species with difficulty.

Several patents, e.g., U.S. Pat. Nos. 3,626,001 and 3,974,214, describe a process for the manufacture of isophthalic acid under much milder conditions. In the process, m-xylene is reacted with molecular oxygen in the presence of an alkanoic acid solvent, e.g., acetic acid, a cobalt catalyst and an alkanal, e.g., acetaldehyde, as promoter; no bromine-containing compound is added and the temperature applied is moderate so that the drawbacks of the former process do not exist. However, the aldehyde is used in relatively large amounts, and it is transformed during the reaction into the corresponding alkanoic acid which must be recovered, purified and commercialized for the process to be economically feasible.

In this latter process also, water is detrimental to the reaction. Still more harmful is phthalic acid produced in the system from o-xylene, which is always present as an impurity in the m-xylene feed. As a consequence, water and phthalic acid must be maintained at low levels, i.e., less than 5 weight percent when the feed is a mixture of m-xylene and m-toluic acid (U.S. Pat. No. 3,626,001, claim 1). This requires that the mother liquors from the separation of isophthalic acid be further processed according to an elaborate procedure which, briefly, comprises the steps of: (1) flashing the solvent which is then submitted to fractional distillation to remove water, (2) adding water to the residue containing the catalysts and contaminants such as phthalic acid, (3) treating the resulting aqueous solution with sodium carbonate to precipitate cobalt carbonate, (4) separating the precipitate from the aqueous solution containing sodium phthalate, and (5) treating the precipitate with acetic acid to regenerate cobalt acetate which then can be recycled (U.S. Pat. Nos. 3,673,154 and 3,919,306).

It is apparent from the foregoing description of the prior art that many of the problems arising in the manufacture of isophthalic acid result from the generalized use of an alkanoic solvent. Actually, for carrying out the transformation of m-toluic acid, which is a relatively high-melting and high-boiling compound, into isophthalic acid, which is an even less volatile and less fusible material, the use of a solvent is an essential requirement for several practical reasons which can be summarized as follows:

(1) Without a solvent, removal of the heat of reaction is made difficult by the tendency of m-toluic acid and isophthalic acid to form crusts and deposits on any cool surface, thereby precluding the use of conventional heat exchangers for controlling temperature.

(2) Without a solvent, the conversion of m-toluic acid into isophthalic acid must be severely limited in order to keep the reaction mixture as a workable slurry.

(3) Without a solvent, handling the reaction mixture and especially separating isophthalic acid therefrom are quite difficult tasks.

(4) Without a solvent, the formation of heavy by-products by condensation and/or addition reactions is generally enhanced, thereby adversely affecting the color and purity of the resulting isophthalic acid.

The solvent used to overcome these difficulties must fulfill a number of conditions. It should dissolve substantial amounts of m-toluic acid at the working temperature but not of isophthalic acid (to allow recovery of the latter by simple solid-liquid separation). It must be inexpensive, inert to oxidation, and sufficiently volatile to allow the removal of the heat of reaction by solvent vaporization. It should be non-corrosive, non-toxic, and it should not interfere with the reaction system. As already noted, acetic acid which is generally used in prior processes is not really inert; it is relatively corrosive, and it is becoming more and more expensive. In these respects, water is a much more attractive solvent. But when water is present in sufficiently great amount to act as a diluent, it generally interferes with the action of metal catalysts, especially cobalt and manganese.

U.S. Pat. No. 2,907,792 describes a process whereby various organic substances can be oxidized by reaction with oxygen in the presence of large amounts of water. For instance, m-toluic acid can be transformed in high yield into isophthalic acid. However, this result is made possible only by the use of hydrogen bromide or other bromine-containing agents at high temperature so that, here again, severe corrosion problems are encountered. Moreover, with this process, non-oxygenated substrates such as xylene are transformed only in poor yield into the corresponding carboxylic acids.

Recently, a process which obviates most of the disadvantages of the prior processes has been described by the applicant for the oxidation of p-toluic acid and mixtures of p-toluic acid with p-xylene and/or other partially-oxidized derivatives thereof such as p-tolualdehyde, (see co-pending application Ser. No. 068,648 filed Aug. 22, 1979). In this process, water is used instead of acetic acid as a solvent in such quantities as to maintain the reaction medium as a homogeneous liquid solution. The conditions are mild despite the fact that no use is made of any promoter. To ensure oxidation in such an aqueous system, the concentration of metal catalyst, i.e., manganese and/or cobalt, must be carefully adjusted so as to be above a well-defined minimum value which depends on the catalyst used and on the composition of the reaction mixture and below a given maximum value. However, if one attempts to apply this process for the oxidation of m-toluic acid, with or without the presence of m-xylene and/or other precursors of isophthalic acid, generally no reaction takes place even when the concentration of catalyst is in close accordance with the requirements of that process.

SUMMARY OF THE INVENTION

It is an object of the present invention to provide an improved process for economically producing isophthalic acid from a substrate which may consist either in m-toluic acid or a mixture thereof with m-xylene and/or other oxygenated derivatives of m-xylene.

It is a further object of this invention to provide a process for carrying out the oxidation of such a substrate in a homogeneous aqueous solution wherein this oxidation is carried out under mild conditions in the absence of any alkanoic acid solvent and of any bromine-containing promoter, thus allowing the use of stainless steel equipment.

Other objects and advantages of the invention will be apparent from a consideration of the following description.

These and other objects of the invention are accomplished by providing a process for the production of isophthalic acid by oxidation of a member of the group comprising m-toluic acid and mixtures thereof with m-xylene and/or other partially-oxidized derivatives of m-xylene with an oxygen-containing gas, said process comprising carrying out this oxidation in a homogeneous aqueous solution containing at least 10 weight percent of water at a temperature of from about 140° C. to 220° C. and under a pressure sufficient to maintain water in the liquid state, in the presence of a catalytically-active metal compound selected from the group comprising manganese compounds and mixtures thereof with cobalt compounds, the concentration of metal compound being at least the amount M in millimoles per kg of reaction mixture given by the following equation:

$$M = \frac{(y + 45.9\, z)(x + 0.0967) + 9.50\, x}{3.02\, x} \quad (1)$$

where
- x is the mole fraction of manganese in the metal catalyst, i.e., Mn/(Mn+Co),
- y is the mole ratio of water to m-toluic acid, and
- z is the mole ratio of dissolved isophthalic acid to m-toluic acid.

Various other features and advantages of this invention will be more fully appreciated from the following detailed description when considered in connection with the accompanying drawings.

DETAILED DESCRIPTION OF PREFERRED EMBODIMENTS

Figure 1:
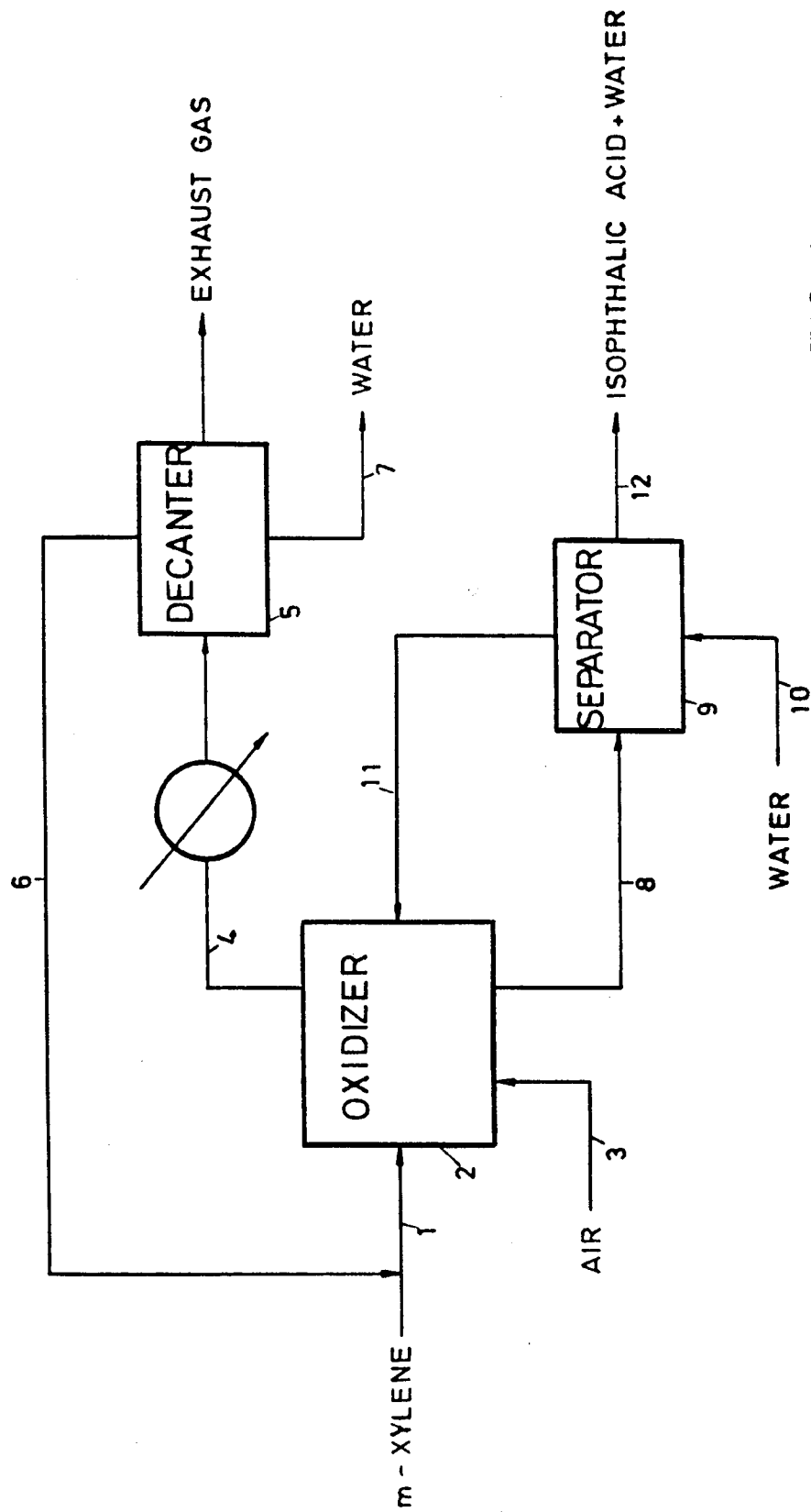
FIG. 1 is a simplified schematic flow diagram of an embodiment of an overall oxidation process including an oxidation step in accordance with the present invention.

It is a fundamental aspect of the present invention that the oxidation of m-toluic acid, whether or not admixed with m-xylene and/or any other oxygenated derivative thereof, can be achieved in the presence of substantial amounts of water as a solvent while using manganese or a mixture of manganese and cobalt as a catalyst provided that the concentration of metal amounts to at least a critical value M which depends on the composition of the reaction mixture according to the foregoing equation (1). This critical value is, therefore, the lowest concentration of catalyst that can be used for a given reaction mixture (for given values of the variables x, y and z). At lower concentrations, no oxidation takes place.

It is preferred in practice to use an amount of catalyst higher than this minimum. If the concentration of catalyst is set closely at the value M as calculated with equation (1), any increase in the variable y, through e.g. accidental increase in the dilution of the system with water, would result in a dramatic breakdown of the reaction. Similarly, an increase of the concentration of dissolved isophthalic acid, resulting from e.g. an accidental increase of temperature, would have the same effect by increasing the value of the variable z. Moreover, it has been observed that the reaction rate is markedly lowered when the concentration of catalyst becomes too close to the minimum value M.

On the other hand, it has been found that concentrations of catalyst higher than about 40 millimoles of metal compound per kg of reaction mixture may also have an adverse effect on the reaction rate, especially when cobalt is present in addition to manganese. Moreover, it is known that when manganese catalysts are used in high concentrations in the presence of water, dark bodies may form which contaminate the desired product of the reaction so as to make it unsuitable for normal application. For these different reasons, the amount of catalyst used will generally be between a value slightly higher than the minimum value M as calculated from equation (1) and about 30 millimoles per kg of reaction mixture.

A surprising feature of this invention is that equation (1) is valid for a wide range of conditions and is independent of important operating variables such as temperature. This is illustrated by the data set forth in the following table wherein experimentally determined values of M are compared with the calculated values from equation (1) for the same reaction mixtures. In considering this data, it must be realized that such determinations of M are subject to experimental errors so that, for a given reaction mixture (i.e., for given values of x, y and z), different values of $M_i$ are expected to be obtained which will statistically be distributed around the actual value with a standard deviation $\sigma$. From the experimental data used to establish equation (1), the standard deviation of such $M_i$ values has been estimated to be 0.6. Accordingly, any experimental value which does not differ from the calculated one by more than twice the standard deviation, i.e., by more than 1.2, can be considered consistent with equation (1).

In practicing the invention, the substrate to be oxidized, e.g., m-toluic acid, is dissolved in water, and the metal catalyst is added to the resulting solution. An oxygen-containing gas is then introduced into this mixture while stirring and maintaining the desired temperature and pressure. As oxidation of the substrate takes place, isophthalic acid is produced and separates as a white crystalline precipitate. Consequently, the concentration of m-toluic acid in the liquid reaction medium decreases and, therefore, the molar ratio of water to m-toluic acid, i.e., variable y in equation (1), increases. By continuing this transformation, a stage would necessarily be reached where the concentration of catalyst would become identical with the minimum concentration M as derived from equation (1), and then oxidation would cease completely. To avoid this situation, isophthalic acid must be removed from the system and

| T °C. | Reaction mixture (% by weight) | | | | x | y | z | M | |
|---|---|---|---|---|---|---|---|---|---|
| | m-xylene | m-toluic acid | isophthalic acid | water | | | | observed | calculated |
| 170 | 0.1 | 19.2 | 0.7 | 80.0 | 1.00 | 31.50 | 0.0285 | 15.0 | 15.1 |
| 170 | 0.0 | 28.7 | 1.2 | 70.1 | 1.00 | 18.49 | 0.0330 | 10.0 | 10.4 |
| 170 | 0.2 | 30.3 | 1.0 | 68.5 | 1.00 | 17.08 | 0.0276 | 10.0 | 9.8 |
| 170 | 0.0 | 34.0 | 4.7 | 61.3 | 1.00 | 13.61 | 0.1120 | 10.0 | 10.0 |
| 170 | 0.3 | 58.1 | 1.2 | 40.4 | 1.00 | 5.26 | 0.0169 | 5.0 | 5.3 |
| 170 | 0.4 | 61.3 | 4.2 | 34.2 | 1.00 | 4.21 | 0.0561 | 5.1 | 5.6 |
| 170 | 0.1 | 21.7 | 1.4 | 76.8 | 0.50 | 26.69 | 0.0523 | 15.0 | 14.6 |
| 170 | 0.0 | 35.6 | 4.0 | 60.4 | 0.50 | 12.81 | 0.0929 | 10.0 | 9.9 |
| 185 | 0.0 | 36.6 | 6.5 | 56.9 | 0.50 | 11.73 | 0.1461 | 10.0 | 10.4 |
| 170 | 0.0 | 42.9 | 4.0 | 53.1 | 0.25 | 9.34 | 0.0771 | 10.0 | 9.1 |
| 170 | 0.2 | 41.4 | 1.3 | 57.1 | 0.17 | 10.41 | 0.0265 | 10.0 | 9.2 |
| 170 | 0.0 | 47.9 | 4.7 | 47.4 | 0.10 | 7.49 | 0.0813 | 10.1 | 10.5 |

As seen in the table and in the examples given hereinafter, the metal catalyst used in the process of the present invention may comprise manganese alone or a mixture of cobalt and manganese. In the case of mixtures of manganese and cobalt, the amount of manganese can be one-tenth the amount of cobalt or even less, but a practical limit is rapidly reached since, as apparent from equation (1), M increases rapidly towards infinity as variable x, i.e., the proportion of manganese in the catalyst), tends to zero. In other words, cobalt alone is inactive, and a decrease in the proportion of manganese must be compensated for by increasing the total concentration of metal. This is in sharp contrast with the teachings of the prior art wherein it is claimed, as a general rule, that cobalt is the best catalyst, especially in the absence of a bromine-containing promoter, and that manganese is less active or inactive. In the present process, cobalt has some enhancing effect upon the reaction rate, but as it is increasingly scarce and expensive, there is no advantage of using an amount of it much in excess of the amount of manganese.

Other metals such as nickel, lead or cerium may also be used, together with cobalt or not, in addition to manganese. Although such other metals are not required for oxidation to take place in a homogeneous aqueous medium, they may afford some practical improvement with respect to product purity and/or reaction rate. Their use is, therefore, intended to be comprised within the scope of the present invention.

The metal compounds added as catalyst in the present process must be soluble in the aqueous reaction mixture, or they must be capable of being transformed into soluble compounds in the mixture. Preferred metal compounds are the salts of carboxylic acids, e.g., the acetates, naphthenates, toluates and the like.

fresh substrate added. This fresh substrate may be m-toluic acid. Another preferred possibility is to produce m-toluic acid "in situ" by adding m-xylene instead.

This operation can be carried out batchwise or continuously. In a preferred embodiment, it is carried out in a continuous flow scheme as shown schematically in the diagram of FIG. 1. In this flow diagram, m-xylene is introduced through line 1 into oxidizer 2 where it is transformed successively into m-toluic acid and isophthalic acid by reaction with oxygen introduced as air through line 3. Oxygen-depleted air leaves the oxidizer through line 4 together with vapors of water and m-xylene which are condensed and then separated in decanter 5. Metaxylene is recycled to the oxidizer through line 6, and water is withdrawn through line 7. The reaction mixture is transferred via line 8 from the oxidizer to separator 9 where precipitated isophthalic acid is separated from the liquid reaction medium. Any solid-liquid separation device can be used for this purpose, but in view of the relatively high temperature and pressure which are applied to maintain the reaction medium as a liquid homogeneous solution, it is preferred to use a settling column wherein isophthalic acid crystals are separated and washed by sedimentation countercurrent to a stream of water from line 10. Water from line 7 can be used except for a purge comprising water of reaction. The water-soluble components of the reaction mixture, i.e., catalysts and intermediate oxidation products, are recycled via line 11 into the oxidizer, while isophthalic acid is recovered from line 12 as a slurry in water. Crude isophthalic acid can then be obtained through e.g. centrifugation and drying. Alternatively, the crude product can be further processed, e.g., by heating the slurry from line 12 until solubilization of the crystals and then recrystallizing purified isophthalic acid upon controlled cooling.

By working in this way, the reaction mixture in the oxidizer progressively approaches a steady state which is characterized by definite contents of the different components of the system, i.e., m-xylene, m-toluic acid, the other oxidation intermediates, isophthalic acid and water, depending on temperature, the rate of feeding with m-xylene and the rate of recycling. In calculating the minimum concentration of catalyst with equation (1) to be used in each case, the variables y and z should correspond to the steady state obtained under the particular conditions utilized.

As can be appreciated from the foregoing description, the transformation of m-xylene and/or m-toluic acid into isophthalic acid according to the process of the present invention does not involve any complicated operation like those required in other processes for the recovery and the purification of an extraneous solvent and/or of the catalyst. No extensive purging of the system is necessary either. The light carboxylic acids formed as by-products, such as formic acid, acetic acid and benzoic acid, are practically inert under the conditions used and may be allowed to accumulate up to relatively high levels without interfering with the reaction. It has been unexpectedly found that phthalic acid, which acts as a harmful poison in most prior art processes, can be tolerated in the present case in substantial amounts, e.g., 10% or even 20% by weight of reaction mixture, as shown in the examples given hereinafter. However, these undesired carboxylic acids should not be allowed to accumulate up to an amount exceeding the amount of water present in the system.

The amount of water to be used in the process of the present invention depends on different factors. As already noted, it is an essential aspect of the present invention that the oxidation be carried out in a homogeneous solution. Otherwise stated, water should not be present in the system as a liquid phase distinct from an organic phase comprising the major part of the substrate to be oxidized. If this should be the case, the oxidation reaction would take place primarily in the organic phase where the concentration of water is relatively small so that the desired solvent effect of water would be partly lost. As a result, the yield of the reaction and the purity of the product would be adversely affected. Moreover, equation (1) generally is not obeyed in such a case. As shown in the examples, much more catalyst then required by equation (1) is needed for allowing oxidation to take place in heterogeneous systems. Therefore, the detrimental effect of too high amounts of catalyst on the reaction rate and product quality are much more likely to be experienced. Still another disadvantage of working with a system comprising a distinct aqueous phase is that, in such a case, phthalic acid acts as a quite harmful poison at levels where it is practically innocuous in homogeneous system. Finally, separation of the reaction mixture into two liquid phases causes difficult technical problems relating to homogeneisation, oxygen dispersion and mass-transfer effects.

For these important reasons, the amount of water is primarily chosen in order than the reaction medium will be a homogeneous aqueous solution, taking into account the other process variables, such as temperature and the relative amounts of the different compounds to be oxidized. For instance, when the process is to be applied to the oxidation of m-toluic acid alone or in admixture with other oxygenated compounds which are relatively soluble in water, such as m-tolualdehyde, the amount of water should be sufficient for the m-toluic acid to be completely dissolved at the working temperature. As the solubility of m-toluic acid in water increases sharply with increasing temperature, the amount of water to be used may be reduced as temperature is increased. As a general rule, however, the amount of water will not be lower than 10% and preferably not lower than 15% by weight of the reaction mixture.

Figure 2:
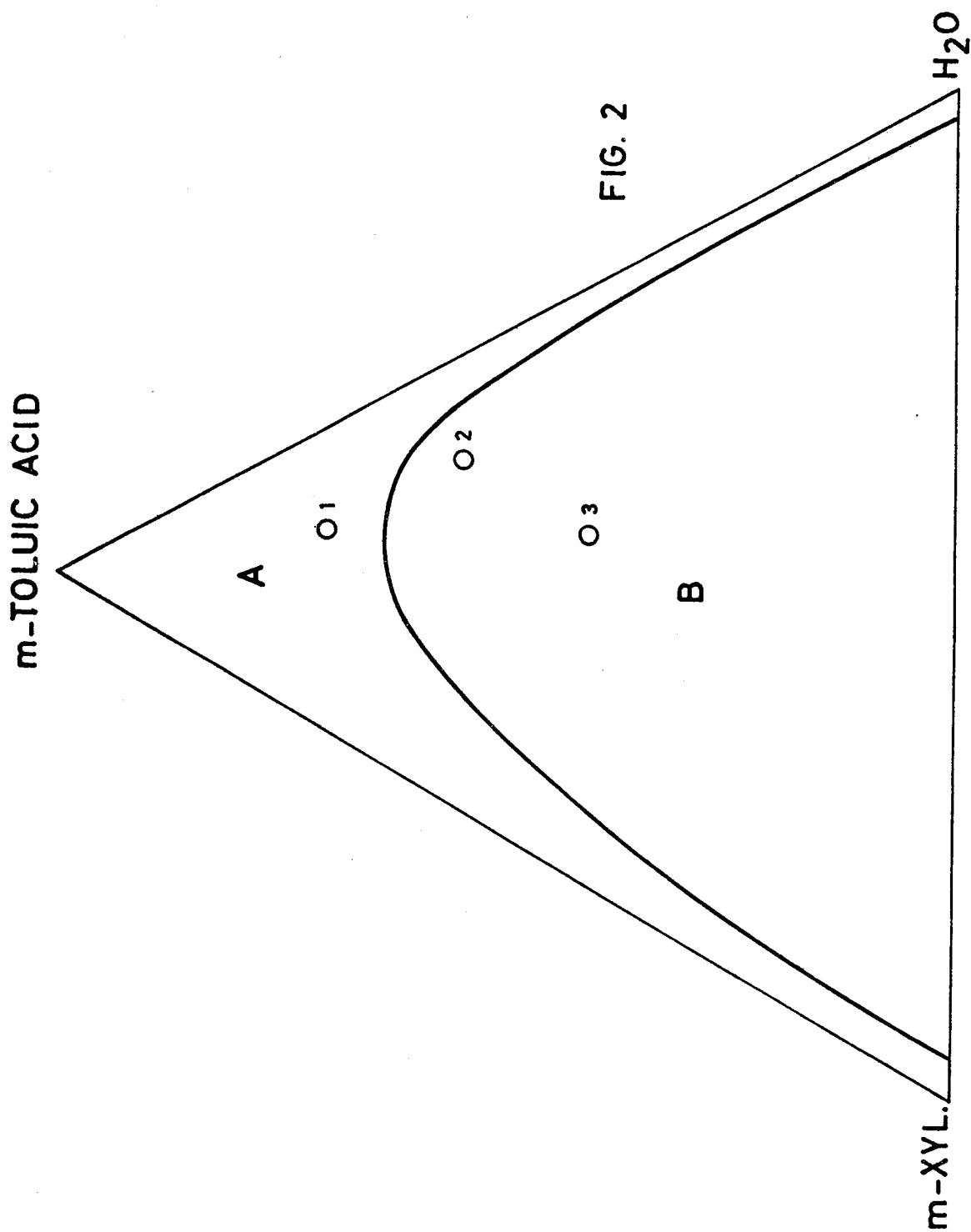
FIG. 2 is a triangular phase diagram for mixtures of m-xylene, m-toluic acid and water at 170° C.

When m-xylene is also a component of the reaction mixture, the amount of water that may be added without inducing phase separation depends on the amount of m-xylene present in the system. FIG. 2 shows a triangular phase diagram for mixtures of m-xylene, m-toluic acid and water at 170° C. In this diagram, A is the zone corresponding to systems forming a homogeneous solution and B is the zone corresponding to biphasic systems. It can be seen that, in order to avoid the presence of a substantial organic phase, the amount of m-xylene present must be limited. The more water present in the system, the more the amount of m-xylene must be restricted. Therefore, when the oxidation of m-xylene according to the process of the present invention is performed batchwise, m-xylene should be added progressively to the reaction mixture, either intermittently or continuously, at such a rate as to maintain the composition of the system in zone A. When, as preferred, the reaction is carried out in a continuous flow scheme as described above with reference to FIG. 1, the molar ratio of m-toluic acid to m-xylene in the reaction mixture at the steady state is generally high, i.e., between 3 and 15, depending mainly upon temperature, so that the conditions required for the reaction medium to form a homogeneous liquid solution are generally fulfilled. At any rate, it is always possible to adjust the temperature and/or the amount of water so as to obtain a homogeneous system in accordance with the present invention.

But other factors must still be taken into account. Thus, as isophthalic acid, the desired product, is of little solubility in the reaction medium, sufficient water must be present to obtain a workable slurry. However, there is no advantage in using such a high amount of water that a substantial part of the isophthalic acid present in the system, e.g., more than 10% thereof, is dissolved at the working temperature. A further limitation results from the effect of water on the reaction rate. Although it is possible, as shown in the foregoing table, to carry out the oxidation in a medium comprising as much as 80 or more percent by weight water, the presence of such high amounts of water may adversely affect the reaction rate. Furthermore, for economic reasons, it is disadvantageous to lose a part of the reactor capacity by using a needlessly large amount of water. For those different reasons, the amount of water in the system should not exceed 75% and preferably 60% by weight of reaction mixture.

The temperature at which the oxidation reaction is carried out is generally at least 140° C. Below this value, it is difficult to maintain the reaction medium as a homogeneous solution. On the other hand, working at temperatures above 220° C. would result in increased overoxidation, undesirable side reactions and corrosion problems. Morever, working at high temperature would result in increasing the amount of dissolved isophthalic acid and this, by raising vehicle z in equation (1), might increase too much the minimum concentration of catalyst to be used.

The pressure is adjusted as a function of temperature. Sufficient pressure should be applied to maintain the reaction medium in the liquid state at the working temperature. An excess of pressure over this value is generally useful for ensuring active oxidation. Generally, the pressure will be between about 5 and about 40 kg/cm².

The invention will now be further described with reference to the following examples which are given for the purpose of illustration only and are not intended to limit the scope of the invention.

EXAMPLE 1

Into a corrosion-resistant autoclave of one-liter capacity equipped with a mechanical agitation device, a heating jacket, a gas inlet tube and a vent, there was charged:
m-toluic acid: 170.3 g,
other oxygenated compounds: 4.7 g,
water: 75.0 g,
manganese acetate: 1.25 mmoles (5 mmoles/kg),
cobalt acetate: 1.25 mmoles (5 mmoles/kg).

In this charge, the water content was 30% by weight or, otherwise expressed, the molar ratio of water to m-toluic acid (variable y in equation (1) hereinabove) was 3.33. The mole fraction of manganese in the catalyst (variable x) was 0.50. As no isophthalic acid was present in the charge, variable z was zero. By application of equation (1), the minimum concentration of catalyst to be used in this case for ensuring oxidation is therefore $$M = \frac{3.33 (0.50 + 0.0967) + 9.50 (0.50)}{3.02 (0.50)} = 4.5 \text{ mmoles/kg}.$$

The actual concentration of catalyst in the charge was 10.0 mmoles/kg, i.e., about twice the minimum amount.

The reactor was pressurized with air to a pressure of 20 kg/cm², and the above mixture was heated while stirring and admitting air at a flow rate of 90 liters per hour (measured at room temperature and atmospheric pressure). Upon heating, the reaction started spontaneously; the temperature rose rapidly and was maintained at 170° C. by controlled cooling.

After 240 minutes of reaction, the absorbed oxygen amounted to 25.9 liters (measured at room temperature and atmospheric pressure). The reaction was then discontinued by cooling; the air flow was stopped, and the autoclave was depressurized. The precipitate contained therein was filtered, washed with water, and dried under vacuum at about 80° C. It was then analyzed by a combination of acidimetry, polarography and vapor-phase chromatography. It was determined that 47.7% of the initial m-toluic acid has been transformed during the reaction into the following products:
isophthalic acid: 80.9 g
3-carboxybenzaldehyde: 3.4 g,
heavy by-products: 4.9 g.

Taking into account that 3-carboxybenzaldehyde and some other intermediate products would in fact be recycled in a continuous process and would ultimately be transformed predominantly into isophthalic acid, it can be estimated that in such a process, the yield of isophthalic acid would amount to about 85 mole percent based on the amount of m-xylene consumed. The value thus estimated may actually be considered, and will be referred to hereinafter as, the selectivity of the transformation for isophthalic acid.

COMPARATIVE EXAMPLE 1.1

The same mixture as in the preceding example was charged except that only 0.50 mmoles each of manganese acetate and cobalt acetate were used. The total concentration of metal catalyst was, therefore, 4.0 mmoles per kg of mixture, i.e., 0.5 mmoles lower than the minimum amount as calculated in the preceding example.

Upon heating this mixture in the presence of a stream of air under the same conditions as in the preceding example, no oxygen absorption took place, even after repeated additions of t-butyl hydroperoxide to initiate the reaction.

This result demonstrates the criticality of the minimum concentration of catalyst as defined in the present invention in successfully oxidizing m-toluic acid in an aqueous medium without resorting to any bromine-containing promoter.

EXAMPLE 2

The experiment of Example 1 was repeated but 2.50 mmoles of manganese acetate were used as catalyst. Oxygen absorption started at 170° C. upon addition of about 0.12 g of t-butyl hydroperoxide to help initiation. After 240 minutes of reaction, oxygen absorbed amounted to 23.0 liters. By treating and analyzing the reaction mixture as in the preceding example, it was determined that 40.5% of the initial m-toluic acid had been transformed during the reaction into the following products:
isophthalic acid: 66.7 g,
3-carboxybenzaldehyde: 4.5 g,
heavy by-products: 3.0 g.

The selectivity of this transformation for isophthalic acid can be estimated to be 84%.

COMPARATIVE EXAMPLE 2.1

The preceding experiment was repeated except cobalt acetate was substituted for manganese acetate. No oxidation took place even after repeated additions of t-butyl hydroperoxide to initiate the reaction.

EXAMPLE 3

The experiment of Example 1 was repeated but with 2.25 mmoles of cobalt acetate and 0.25 mmoles of manganese acetate as catalyst. Oxygen absorption started spontaneously and after 240 minutes of reaction amounted to 30.8 liters. By treating and analyzing the reaction mixture as already described, it was determined that 52.0% of the m-toluic acid fed had been transformed during the reaction into the following products:
isophthalic acid: 87.5 g,
3-carboxybenzaldehyde: 4.4 g,
heavy by-products: 1.5 g.

The selectivity of this transformation for isophthalic acid can be estimated to be 85%.

By comparing these results with those of the preceding examples, it appears that although cobalt alone is unable to catalyze the oxidation of m-toluic acid to isophthalic acid in aqueous medium, cobalt has a beneficial effect upon the initiation and the rate of this reaction when used in conjunction with even small amounts of manganese.

EXAMPLE 4

Into the same autoclave as in the preceding examples there was charged:
m-toluic acid: 121.7 g,
other oxygenated compounds: 3.3 g,
water: 125.0 g,
manganese acetate: 1.875 mmoles (7.5 mmoles/kg),
cobalt acetate: 1.875 mmoles (7.5 mmoles/kg).

In this charge, the water content was, therefore, 50% by weight, and the variables x, y and z of equation (1) were 0.50, 7.76 and 0, respectively. Therefore, the minimum concentration of catalyst calculated with the equation is:

$$M = \frac{7.76 (0.50 + 0.0967) + 9.50 (0.50)}{3.02 (0.50)} = 6.2 \text{ mmoles/kg}$$

The actual concentration of the catalyst in the charge was 15.0 mmoles/kg, i.e., 2.4 times the minimum amount.

Air was admitted into the reactor, and the mixture was heated while stirring as in the preceding examples. Oxygen absorption started spontaneously and took place actively, bringing about a rapid increase of temperature which was maintained at 185° C. by controlled cooling.

After 240 minutes of reaction, the absorbed oxygen amounted to 24.3 liters. The reaction was then discontinued, and the resulting mixture was treated and analyzed as described in Example 1. It was thus determined that 59.0% of the initial m-toluic acid had been transformed during the reaction into the following products:
isophthalic acid: 72.7 g,
3-carboxybenzaldehye: 3.6 g,
heavy by-products: 1.3 g.

The selectivity of this transformation for isophthalic acid, i.e., the molar yield that can be expected for a continuous process wherein 3-carboxybenzaldehyde would be recycled, can be estimated to be 87%.

EXAMPLE 5

Into the same autoclave as in the preceding examples, there was charged:
m-xylene: 25.0 g,
m-toluic acid: 171.1 g,
other oxygenated compounds: 3.9 g,
water: 50.0 g,
manganese acetate: 1.25 mmoles (5 mmoles/kg),
cobalt acetate: 1.25 mmoles (5 mmoles/kg).

This charge has a water content of 20% by weight; nevertheless, as shown by the diagram of FIG. 2 (point 1), it forms a homogeneous solution when heated up to 170° C. By application of equation (1) to this solution, the minimum concentration of catalyst to be used for ensuring oxidation therein is calculated to be M=4.0 mmoles/kg. Actually, the concentration of metal was 10.1 mmoles/kg, i.e., 2.5 times this minimum concentration.

The reactor was pressurized with air up to a pressure of 20 kg/cm², and the above mixture was heated while stirring and admitting air at a flow rate of 120 liters per hour (measured at room temperature and atmospheric pressure). Oxygen absorption started spontaneously, bringing about a rapid increase of temperature which was maintained at 170° C. by controlled cooling. After 240 minutes of reaction, oxygen absorbed amounted to 35.3 liters. The admission of air was then discontinued, and the reactor was progressively depressurized so as to cover unreacted m-xylene by stripping with water. The reactor was finally cooled and opened. The precipitate contained therein was then recovered and analyzed as described in Example 1. It was thus determined that 93.5% of the m-xylene fed and 34.5% of the m-toluic acid fed had been transformed during the reaction into the following products:
isophthalic acid: 79.6 g,
3-carboxybenzaldehyde: 7.0 g,
other intermediates: 0.2 g,
heavy by-products: 5.3 g.

The selectivity of this transformation for isophthalic acid can be estimated to be 82%.

COMPARATIVE EXAMPLE 5.1

The same mixture as in Example 5 was charged except that only 0.375 mmoles each of manganese and cobalt was used. The total concentration of metal catalyst was, therefore, 3.0 mmoles/kg, i.e., 1.0 mmole lower than the minimum amount as calculated in Example 5.

Upon heating this mixture in the presence of a stream of air under the same conditions as described in Example 5 hereinabove, oxygen absorption took place spontaneously but after about 30 minutes fell down to a negligible level. Nevertheless, heating was continued at 170° C. until a total reaction time of 240 minutes had elapsed as in Example 5. At that time, the absorbed oxygen amounted to 6.6 liters, i.e., only 19%, of the absorption recorded in Example 5. By treating and analyzing the resulting reaction mixture as described in Example 5, it was determined that 31.4% of the starting m-xylene and only 4.4% of the starting m-toluic acid had been transformed during the reaction into the following products:
isophthalic acid: 4.5 g,
3-carboxybenzaldehyde: 4.4 g,
other intermediates: 1.7 g,
heavy by-products: 1.2 g.

By comparing these results with those of Example 5 hereinabove, it can be concluded that the transient oxygen absorption observed in the beginning of the experiment corresponded mainly to the transformation of some m-xylene with very little formation of isophthalic acid.

This comparative example thus shows clearly that the production of isopthalic acid in aqueous medium from a mixture of m-xylene and m-toluic acid as practiced in the present process is not feasible when the concentration of catalyst is even slightly lower than required by equation (1) in accordance with the present invention.

COMPARATIVE EXAMPLE 5.2

The same experiment as described in Example 5 was carried out with the following charge:
m-xylene: 25.0 g,
m-toluic acid: 134.4 g,
other oxygenated compounds: 3.1 g,
water: 87.5 g,
manganese acetate: 1.25 mmoles,
cobalt acetate: 1.25 mmoles.

It can be seen that this mixture is the same as the charge of Example 5, except that 37.5 g of water have been substituted for about the same amount of m-toluic acid. As a result, the mixture no longer forms a homogeneous solution at 170° C.; instead, a biphasic mixture is produced as shown in FIG. 2 (point 2).

Oxygen absorption started spontaneously upon heating, and the reaction was continued while maintaining the temperature at 170° C. After 240 minutes of reaction, the absorbed oxygen amounted to 18.6 liters, i.e., roughly half that in Example 5. Moreover, upon analysis of the reaction mixture, it was determined that only 76.8% of the starting m-xylene and 16.8% of the starting m-toluic acid had been transformed during the reaction into the following products:
isophthalic acid: 28.2 g,
3-carboxybenzaldehyde: 6.9 g,
other intermediates: 0.5 g,
heavy by-products: 2.8 g.

From these data, it can be estimated that the selectivity of the transformation for isophthalic acid was 72% instead of 82% in Example 5.

Thus, not only the rate of the reaction but also its selectivity for the desired product is substantially lower when the reaction mixture comprises two immiscible liquid phases at the working temperature instead of being a homogeneous solution in accordance with the present invention.

COMPARATIVE EXAMPLE 5.3

This example illustrates the fact that equation (1) giving the minimum concentration of catalyst to be employed in accordance with the present invention is not obeyed when the reaction mixture comprises two immiscible liquid phases as in the preceding comparative example.

Into the same autoclave as in the preceding examples, there was charged:
m-xylene: 58.0 g,
m-toluic acid: 102.6 g,
other oxygenated compounds: 2.4 g,
water: 87.0 g,
manganese naphthenate: 0.44 mmoles (1.76 mmoles/kg),
cobalt naphthenate: 4.36 mmoles (17.44 mmoles/kg).

As can be seen from FIG. 2 (point 3), such a mixture comprises a substantial organic phase even when heated at 170° C. The concentration of metal catalyst in the whole system was 19.2 mmoles/kg, i.e., 2.6 times the minimum concentration calculated from equation (1), assuming this to be valid for such a system.

The reactor was pressurized with air to a pressure of 20 kg/cm$^2$, and the above mixture was heated while stirring and admitting air at a flow rate of 177 liters per hour. Oxygen absorption started spontaneously, but after 60 minutes of reaction at about 170° C., it fell down to a negligible level. Oxygen then absorbed amounted to only 10.5 liters.

COMPARATIVE EXAMPLE 5.4

The experiment of the preceding comparative example was repeated with 2.50 mmoles each of manganese and cobalt acetate as catalyst. The concentration of metal catalyst was, therefore, 20.0 mmoles/kg, i.e., 3.5 times the minimum concentration calculated from equation (1).

Again, oxygen absorption started spontaneously upon heating, but in this case no breakdown in the reaction rate was observed. The reaction was, therefore, continued while maintaining temperature at 170° C. After 240 minutes of reaction, oxygen absorbed amounted to 36.7 liters. The admission of air was then discontinued and the same procedure as described in Example 5 was used to analyze the reaction mixture. It was thus determined that 74.2% of the m-xylene fed had been transformed during the reaction into the following products:
isophthalic acid: 33.2 g,
3-carboxybenzaldehyde: 5.4 g,
other intermediates including m-toluic acid: 6.1 g,
heavy by-products: 3.0 g.

From these data, it can be estimated that the selectivity of the transformation for isophthalic acid was only 66%, i.e., even less than in Comparative Example 5.2.

This comparative example confirms that although oxidation can be achieved in a biphasic system by significantly increasing the amount of catalyst, the selectivity for isophthalic acid is definitely lower than when the reaction is carried out in a homogeneous solution in accordance with the present invention.

EXAMPLE 6

The experiment of Example 5 was repeated but 62.5 g of phthalic acid were added to the charge; the phthalic acid content of the resulting mixture was, therefore, nearly 20% by weight.

Oxygen absorption started spontaneously upon heating, and the reaction was continued while maintaining a temperature of 170° C. After 240 minutes of reaction, the absorbed oxygen amounted to 31.2 liters, i.e., almost the same amount as in Example 5.

This example shows that in the process of the present invention, the presence of phthalic acid is not detrimental as it is in most processes of the prior art.

COMPARATIVE EXAMPLE 6.1

The same biphasic mixture as in Comparative Example 5.2 was used as charge but 62.5 g of phthalic acid were added thereto. The phthalic acid content of the resulting mixture was 20% by weight as in the preceding example.

Upon heating this mixture for 240 minutes at 170° C. in the presence of a stream of air under the same conditions as in the preceding example, no oxygen absorption took place even after repeated additions of t-butyl hydroperoxide to initiate the reaction.

This example shows that phthalic acid is a powerful inhibitor of oxidation when the mixture to be oxidized is a biphasic system instead of being a homogeneous solution in accordance with the present invention.

The foregoing examples clearly demonstrate that in contrast to the explicit teachings of the prior art, water can be used as a solvent for the production of isophthalic acid by oxidation of m-toluic acid or a mixture of m-toluic acid with m-xylene and/or other partially-oxidized derivatives of m-xylene. By using water in large amounts (not less than about 10% by weight of the reaction mixture) to form a homogeneous aqueous solution of the substrate and by adding an amount of manganese-containing catalyst in excess of the critical value M given by equation (1), the substrate is actively oxidized to isophthalic acid under mild conditions.

The foregoing embodiments have been set forth as examples of the invention and are not intended to be limiting. Since modifications of the disclosed embodiments within the scope and spirit of the invention may occur to persons skilled in the art, the scope of the invention is to be limited solely by the scope of the following claims:

What is claimed is:

1. Process for producing isophthalic acid comprising oxidizing a substrate selected from the group consisting of m-toluic acid and mixtures of m-toluic acid with m-xylene and/or other partially-oxidized derivatives of m-xylene with an oxygen-containing gas in a homogeneous aqueous solution comprising at least 10 weight percent water at a temperature of from about 140° C. to 220° C. and a pressure sufficient to maintain some of the water in the liquid state, in the presence of a catalytically active metal compound selected from the group consisting of manganese compounds and mixtures of manganese compounds with cobalt compounds; the concentration of metal compounds being at least the amount M in millimoles per kilogram of reaction mixture given by the following equation:

$$M = \frac{(y + 45.9 z)(x + 0.0967) + 9.50 x}{3.02 x}$$

where x is the mole fraction of manganese in the metal catalyst, y is the mole ratio of water to m-toluic acid, and z is the mole ratio of dissolved isophthalic acid to m-toluic acid.

2. Process according to claim 1 wherein the concentration of catalyst is less than about 40 millimoles of metal compound per kilogram of reaction mixture.

3. Process according to claim 2 wherein the concentration of catalyst is less than about 30 millimoles of metal compound per kilogram of reaction mixture.

4. Process according to claim 1 wherein the catalyst comprises a mixture of a manganese compound and a cobalt compound; the number of millimoles of manganese compound being not less than the number of millimoles of cobalt compound.

5. Process according to claim 1 wherein the catalyst comprises at least one metal salt of a carboxylic acid.

6. Process according to claim 1 wherein water comprises from about 10 to about 80 weight percent of the reaction mixture.

7. Process according to claim 6 wherein water comprises from about 15 to about 75 weight percent of the reaction mixture.

8. Process according to claim 7 wherein water comprises from about 15 to about 60 weight percent of the reaction mixture.

9. Process according to claim 1 wherein the pressure lies in the range from about 5 to about 40 kg/cm$^2$.

10. Process according to claim 1 wherein the reaction mixture is substantially free of extraneous organic solvent.

11. Process according to claim 1 further comprising the additional steps of transferring the reaction mixture resulting from the oxidation of the homogeneous aqueous solution to a settling column, separating and washing crystals of isophthalic acid from the mixture by sedimentation countercurrent to a stream of water; recovering water-soluble components from the reaction mixture and recycling them to the oxidation step; recovering an aqueous slurry of isophthalic acid crystals from the settling column; and separating the isophthalic acid crystals from the recovered slurry.

* * * * *